United States Patent
Derbyshire et al.

(10) Patent No.: US 6,232,485 B1
(45) Date of Patent: May 15, 2001

(54) PRODUCTION OF PHOSPHATE ESTERS

(75) Inventors: Tracy Anne Derbyshire, Davyhulme; Hazel May Farrow, Hough Green; Jonathan Simon Hill, Flixton, all of (GB)

(73) Assignee: Great Lakes Chemical Corporation, West Lafayette, IN (US)

(*) Notice: Subject to any disclaimer, the term of this patent is extended or adjusted under 35 U.S.C. 154(b) by 0 days.

(21) Appl. No.: 09/341,010

(22) PCT Filed: Oct. 28, 1998

(86) PCT No.: PCT/GB98/03225

§ 371 Date: Nov. 26, 1999

§ 102(e) Date: Nov. 26, 1999

(87) PCT Pub. No.: WO99/21863

PCT Pub. Date: May 6, 1999

(30) Foreign Application Priority Data

Oct. 29, 1997 (GB) .................................................. 9722719

(51) Int. Cl.⁷ ........................................................ C07F 9/12
(52) U.S. Cl. .......................... 558/102; 558/92; 568/785; 568/789; 568/790
(58) Field of Search ........................................ 558/92, 102

(56) References Cited

U.S. PATENT DOCUMENTS

| 3,014,079 | 12/1961 | Olin . |
| 3,859,395 | 1/1975 | Terhune et al. ........................ 260/966 |
| 4,093,680 | 6/1978 | Randell et al. ........................ 260/966 |
| 4,414,161 | 11/1983 | Giolito ................................. 260/975 |
| 5,206,404 | 4/1993 | Gunkel et al. ........................ 558/146 |

FOREIGN PATENT DOCUMENTS

| 0001698 A1 | 2/1979 | (EP) . |
| 0249415 A2 | 12/1987 | (EP) . |
| 1060156 | 3/1967 | (GB) . |
| 1228549 | 4/1971 | (GB) . |
| 1235240 | 6/1971 | (GB) . |
| 2007224 | 5/1979 | (GB) . |
| 2012271 | 7/1979 | (GB) . |

*Primary Examiner*—Michael G. Ambrose
(74) *Attorney, Agent, or Firm*—Woodard, Emhardt, Naughton, Moriarty & McNett

(57) ABSTRACT

A process for the production of liquid meta-rich triaryl phosphate esters having low triphenyl phosphate content and low viscosity comprises (a) an alkylation stage wherein a phenol is reacted with an olefin having 2 to 12 carbon atoms in the presence of a strong acid catalyst to give a reaction product comprising a mixture of meta and para alkylated phenols; and (b) a transalkylation stage wherein the mixture of alkylated phenols from the alkylation stage is heated in the presence of a strong acid catalyst to increase the meta isomer content of the mixture to at least 25% whilst maintaining a phenol level below 22%; and (c) a phosphorylation stage wherein the mixture of alkylated phenols from the transalkylation stage is reacted with a phosphorylating agent; and wherein the strong acid catalyst used in stages (a) and (b) is a Bronsted acid having an acid strength of less than zero. Preferred catalysts are activated clays such as bentonite, montmorillonite or Fullers Earth clay. The alkylation and transalkylation are conducted at temperatures between 100° C. and 200° C., preferable 150° C. and 180° C.

18 Claims, No Drawings

PRODUCTION OF PHOSPHATE ESTERS

This invention relates to the production of liquid triaryl phosphate esters. More particularly, this invention relates to the production of liquid meta/para isomer triaryl phosphate esters containing a low concentration of triphenyl phosphate and having good liquid properties.

Mixed synthetic triaryl phosphate esters are prepared by alkylating phenol with alkenes such as propylene and butylene to produce a mixture of phenol and alkyl substituted phenols which is commonly referred to as alkylated phenol. This alkylated phenol may be reacted directly with a phosphorylating agent such as phosphorus oxychloride to produce a mixed triaryl phosphate ester. Such processes are widely practised and well known in the art. They are described for example in U.S. Pat. No. 4,093,680.

The composition of the triaryl phosphate ester product is related to the composition of the alkylated phenol feedstock. If the phenol is completely alkylated the alkylate is free from phenol and the phosphate is free from triphenyl phosphate. However, such a product would be very viscous or solid and thereby unsuited for many of the applications in which triaryl phosphate esters find use. A general principle, well known to those skilled in the art, is that the liquid properties, as exemplified by viscosity, may be modified by varying the amounts of the different components of the phenolic feedstock. In certain applications, it is important to have good liquid properties (ie low viscosity) but at the same time not have a high concentration of triphenyl phosphate in the final phosphate ester mixture. There are a number of reasons why a low triphenyl phosphate content (less than 2%) may be desirable. These include improved thermal stability; improved hydrolytic stability; reduced stress cracking in plastics; lower volatile loss and reduced volatility, in particular reduced tendency for flashing in high temperature applications (where flashing is a generation of flame). U.S. Pat. No. 5,206,404 describes processes for the production of liquid triaryl phosphate esters comprising less than 2% triphenyl phosphate by a process of distilling a typical mixed triaryl phosphate ester under particular conditions so as to remove a volatile fraction and leave a liquid residue which is the product. Whilst U.S. Pat. No. 5,206,404 states that it is impossible to produce a liquid phosphate of this type by direct phosphorylation of an alkylated phenol one object of the present invention is to provide a process of producing a liquid phosphate ester having a low content of triphenyl phosphate and good liquid properties by the direct phosphorylation of an alkylated phenol.

Using a standard raw material feedstock mixture, eg phenol/t-butyl phenol, a triaryl phosphate of low triphenyl phosphate content is obtained by reducing the proportion of phenol in the feedstock, eg to 20:80. However, the resulting phosphate can be very viscous or even solid and thus unsuitable for many applications. In order to improve the physical properties of liquid phosphate esters of low triphenyl phosphate content, the composition of the feedstock can be modified such that there is an increase in the amount of meta substituted alkylated phenols present in the feedstock. U.S. Pat. No. 4,414,161 describes a process for the production of low temperature stable liquid phosphate esters which comprises the steps of butylating phenol to produce a p-tertiary butyl phenol, catalytically isomerising said p-tertiary butyl phenol to produce a mixture of para and meta tertiary butyl phenols (which isomerisation also dealkylates a proportion of the tertiary butyl phenol); realkylating the product to produce a mixed meta and para tertiary butyl phenol which is then phosphorylated to produce a triaryl phosphate ester. The processes described in U.S. Pat. No. 4,414,161 produce no meta tertiary butyl phenol in the first stage of the reaction, a product comprising 19.11% of meta tertiary butyl phenol, 30.52% of para tertiary butyl phenol and 43.32% of phenol at the end of the isomerisation step and 16.18% meta, 45.24% para and 30.34% phenol at the end of the realkylation step.

As indicated above, the process for preparing the alkylated phenol feedstock of U.S. Pat. No. 4,414,161 requires three steps, namely alkylation, isomerisation (or transalkylation) and realkylation. A further object of the present invention is to provide a process for the production of liquid phosphate esters which does not require a realkylation step in the preparation of the alkylated phenol.

Furthermore, the alkylated phenol product obtained by the process of U.S. Pat. No. 4,414,161 contains greater than 30% phenol and yet only has around 16% of meta alkylated phenol. In order to generate a phosphate ester containing less than 2% triphenyl phosphate and with good liquid properties, the alkylated phenol feedstock must contain less than 22% phenol and greater than 20% meta-t-butyl phenol. 30% phenol is considered too high a content for obtaining a phosphate ester with acceptable triphenyl phosphate content. Yet another object of the present invention is to provide a process for the production of liquid phosphate esters in which the phenol content and meta isomer content of the alkylated phenol feedstock is such as to obtain a phosphate ester containing less than 2% triphenyl phosphate.

U.S. Pat. No. 4,492,660, U.S. Pat. No. 3,014,079 and GP 1060156 also describe the use of catalysts to obtain meta-alkylated phenols.

According to the present invention there is provided a process for producing a liquid traryl phosphate ester of low triphenyl phosphate content and low viscosity comprising (a) an alkylation stage wherein a phenol is reacted with an olefin having 2 to 12 carbon atoms in the presence of a strong acid catalyst to give a reaction product comprising a mixture of meta and para alkylated phenols; and (b) a transalkylation stage wherein the mixture of alkylated phenols from the alkylabon stage is heated in the presence of a strong acid catalyst to increase the meta isomer content of the mixture to at least 20% whilst maintaining a phenol level below 22%; and (c) a phosphorylation stage wherein the mixture of alkylated phenols from the transalkylation stage is reacted with a phosphorylating agent; and wherein the strong acid catalyst used in stages (a) and (b) is a Bronsted acid having an acid strength of less than zero.

The use of selected acidic catalysts leads to the formation of an alkylated phenol containing a high proportion of the meta alkylated phenol. As stated above such acids are Bronsted acids having an acid strength of less than zero. Acid strength Ho is defined by the equation $$Ho = pK_a + \log \frac{[B]}{[BH^+]}$$

where [B] and [BH+] are the concentrations of the neutral base and its conjugate acid respectively. The acid strength may be measured by the use of suitable indicators.

The acid strength is an expression of the ability of an acid to charge a neutral organic base. This charge can occur by transfer of a proton from a Bronsted acid or by transfer of an electron pair from a Lewis acid. Where the catalyst is a solid with a distribution of sites having different acid strengths those useful in this invention have at least some Bronsted acid sites having an acid strength of less than zero.

The preferred olefins for use in the processes of this invention are propylene, n-butylene and isobutylene. The most preferred olefin is isobutylene.

The nature of the catalyst plays a crucial role in determining the composition of the alkylated phenol product. The catalysts conventionally used are Lewis acids such as aluminium chloride and magnesium chloride which lead to the formation of little or no meta alkylated phenol. U.S. Pat. No. 4,492,660 describes the use of trifluoromethane sulphonic acid which is a Bronsted acid having an acid strength of less than zero to catalyse the reaction between phenol and isobutylene. However this reaction produces no meta alkyl phenol under the reaction conditions which are disclosed. We have found that the Bronsted acid catalysts having an acid strength of less than zero and in particular acid activated clays such as acid activated bentonite, montmorillonite and Fullers Earth; heteropolyacids such as phosphotungstic acid and trifluoromethane sulphonic acid can, if used in appropriate quantities and under appropriate conditions, lead to the production of an alkylated phenol comprising greater than 5% of meta alkylated phenol and preferably greater than 10%, 15% or even 20% by weight of meta alkylated phenol. Preferred catalysts are solid materials which can be readily separated from the reaction products and recycled for further use. Also preferred are acid catalysts which have an acid strength of less than minus 3 and the most preferred are those having an acid strength of less than minus 8. The preferred homogeneous catalysts are those which have an acid strength of less than minus 8. The heterogeneous catalysts such as the acid activated clays may have an average acidity measured over the whole surface outside the preferred ranges and still be useful apparently by virtue of their having some sites which have an acidity within the preferred ranges. The heterogeneous catalysts are preferred as they may be active at lower acidity values and are more easily separated from the product.

The term "heteropolyacids" is used in this specification to define acids of the type described by I. V. Kozhevnikov in Catalyst Review—Science and Engineering Volume 37(2) page 311. The preferred heteropolyacid for use in the processes of this invention is phosphotungstic acid. This and certain other of the heteropolyacids are liquid and their use would result in a homogeneous process which would require further processing to separate the catalyst. For this reason we prefer to use a solid form of the catalyst which can be separated by filtration. In the case of the heteropolyacids the metal salts may be solid or less preferably the acid itself can be supported on an inert solid. The cesium salt of phosphotungstic acid are solids and their use as a catalyst forms a preferred aspect of the present invention, especially the salts having the formula $Cs_{2.0-2.6}H_{0.4-1.0}PW_{12}O_{40}$.

As well as the supported heteropolyacids and acid treated clays, a variety of other heterogeneous catalysts are potentially useful in the processes of this invention. Examples are ion exchange resins such as those sold under the Trade Mark Nafion; fluorided silicas/aluminas and fluorided aluminas; Supported phosphoric and sulphuric acids (on supports such as silica or diatomaceous earth); Supported antimony pentafluoride and sulphated zirconia or titania. The utility of any of these materials may be determined by experiment.

The quantity of catalyst which is employed can exert an influence upon the composition of the alkylate. In general we prefer to utilise at least 0.25% (by weight of the phenol) of the catalyst, usually at least 1.0% and preferably at least 2.5% by weight. The minimum amount of catalyst needed to produce an alkylate having the desired proportion of meta alkylated phenol may be determined by routine experiment. Not all Bronsted acids having an acid strength of less than zero are effective catalysts. The effectiveness of particular catalysts may be determined by empirical means.

The reaction temperature at which the alkylation is carried out is also a significant factor in influencing the composition of the product. Generally we prefer that the reaction is carried out at a temperature of the range 100° C. to 200° C., and more preferably at a temperature of the range 150° C. to 180° C.

The alkylation reaction may conveniently be carried out by adding the olefin continuously to the bulk of the phenol over the course of the reaction. Typical reaction times are in the range 1 to 4 hours.

The alkylation reaction may be terminated following the completion of the olefin addition. By suitable optimisation of catalyst and reaction temperature it may be possible to obtain an alkylated phenol comprising 20% or more of meta alkylated phenol. More usually the content of meta alkylated phenol is in the range 15 to 25%. The balance of the alkylated phenol comprises para alkylated phenols (usually 40 to 60%); unreacted phenol (10 to 20%) and smaller quantities of 2,4 di alkyl and 3,5 di alkyl phenols. These alkylated phenols may be converted into triaryl phosphate esters using conventional phosphorylation processes. However we have also found that the proportion of meta alkylated phenols produced may be increased further and that the alkylated phenols produced form a preferred feedstock for the production of triaryl phosphate esters. The same reaction conditions and catalysts useful in the alkylation reaction have been found to be useful in promoting the transalkylation of para alkyl phenols into meta alkyl phenols without any significant degree of dealkylation taking place.

The catalysts, catalyst concentrations and reaction temperatures which have been found to be useful in the alkylation process also have been found to be useful in the transalkylation process. The preferred alkylated phenol starting material is one which has been produced by the alkylation processes as herein before described. It is thereby preferred if only for reasons of convenience to carry out the alkylation and the transalkylation steps under substantially the same conditions and using the same catalyst. The two process steps are preferably carried out in a single processing step without any attempt to isolate an intermediate alkylated phenol product. The amount of meta alkyl phenol may be increased in the transalkylation step perhaps to a level as high as 35% without any significant increase in the amount of phenol present. However, the transalkylation is preferably carried out under conditions which minimise the increase in phenol concentration caused by the dealkylation of alkylated phenol and is preferably terminated if significant quantities of dealkylation are found to occur. The transalkylation reaction generally requires a reaction time of at least 1 hour and probably less than 4 hours. The alkylate is maintained under the reaction conditions for a period of at least one hour after the addition of olefin has been completed. In the most preferred embodiment the alkylate is maintained under same conditions and in the presence of the same catalyst after the addition of the olefin has been completed. Also, in some instances, the alkylation and transalkylation take place concurrently.

After the transalkylation has been completed, the alkylate may be used directly in the production of a triaryl phosphate ester. It may be preferable and convenient to separate the alkylate from the catalyst prior to the phosphorylation step. For this reason the use of solid catalyst such as the acid Alkylation and Transalkylation The efficiency of a series of catalysts in promoting the alkylation of phenol with isobutylene was evaluated using following techniques:

1. 616 g molten phenol was added to a 2 litre glass flask.
2. The appropriate amount of catalyst as indicated in Table 1 was added.

The mass was slowly heated to 160° C., using Nitrogen purge to maintain inert atmosphere. At 160° C. isobutylene gas was added to the mass at a rate of 800–900 cc/min for 2.5 hours until the mixture had taken up approximately 300 g butylene (the rate of addition was such that no significant quantity of gas was seen to bubble off .) A sample of alkylated phenol was removed and analysed. The analysis is reported in Table 1 in the columns headed "alkyl".

The mass was then stirred at 160° C. for a further 3 hours to transalkylate the mass.

3. The reaction mass was then cooled to approximately 50° C. and discharged from the vessel. The catalyst was removed by filtration. A sample was analysed and the analysis is reported in Table 1 in the columns headed "transalkyl".

The results of the experiments are set out in Table 1.

TABLE 1

| Catalyst | Catalyst Level (% w/w) | % Phenol | | % Para t-butyl Phenol | | % Meta t butyl phenol | | % 2,4 di t-butyl phenol | | % 3,5 di t butyl phenol | |
|---|---|---|---|---|---|---|---|---|---|---|---|
| | | Alkyl | Transalkyl | Alkyl | Transalkyl | Alkyl | Transalkyl | Alkyl | Transalkyl | Alkyl | Transalkyl |
| Fittrol F-ILM* | 2.6 | 15.72 | 19.57 | 55.7 | 37.92 | 17.1 | 29.26 | 5.37 | 2.0 | 2.53 | 8.0 |
| $AlCl_3$ | 2.6 | 21.18 | 18.71 | 44.42 | 53.99 | 0.51 | 0.7 | 19.67 | 12.76 | 0.05 | 0 |
| $AlCl_3$ | 5 | 10.31 | 7.79 | 67.95 | 60.23 | 1.38 | 1.16 | 15.04 | 9.57 | 0.09 | 0 |
| $SnCl_2$ | 2.6 | 17.93 | 13.8 | 54.7 | 67.76 | 0.24 | 0.41 | 22.16 | 13.96 | 0 | 0 |
| Para toluene sulphonic acid | 2.6 | 15.33 | 9.83 | 46.15 | 68.34 | 0.35 | 0.6 | 27.4 | 17.28 | 0 | 0 |
| $TiCl_4$ | 0.65 | 89.18 | 90.44 | 5.93 | 5.38 | 0.03 | 0.03 | 0.52 | 0.45 | 0.01 | 0 |
| $H_2SO_4$ (98%) | 2.6 | 14.06 | 13.25 | 66.9 | 72.06 | 0.6 | 1.1 | 14.04 | 10.13 | 0 | 0 |
| Amberlyst 15 ion exchange resin | 2.6 | 29.42 | 25.3 | 29.59 | 41.7 | 0.08 | 0.06 | 20.22 | 18.22 | 0.01 | 0.01 |
| Cesium Salt of phosphotungstic heteropolyacid** | 2.6 | 13.63 | 16.66 | 47.688 | 38.97 | 22.63 | 25.6 | 4.56 | 2.51 | 6.9 | 11.08 |
| Trifluoromethane-sulfonic acid | 1.6 | 8.7 | 14.36 | 53.3 | 31.24 | 19.16 | 29.25 | 7.74 | 1.63 | 6.43 | 18.32 |
| Trifluoromethane-sulfonic acid | 0.8 | 16.22 | 19.36 | 61.86 | 45.32 | 11.55 | 22.44 | 5.47 | 2.33 | 1.56 | 7.15 |
| Trifluoromethane-sulfonic acid | 0.4 | 16 | 17.82 | 67.11 | 57.9 | 6.38 | 14 | 6.89 | 4.38 | 0.46 | 2.5 |
| Trifluoromethane-sulfonic acid | 2 × 0.1 | 15.77 | 23.74 | 69.2 | 48.76 | 1.6 | 15.33 | 10.12 | 3.55 | 0 | 2.89 |

**This salt was $C_{2.5}H_{0.5}PW_{12}O_{40}$
*This is an acid activated montmorillonite clay.
Notes
1) Only 0.65% $TiCl_4$ was used as this catalyst was very reactive with water/air and handling was difficult.

activated clays or the metal salts of the heteropolyacids is preferred as they can be separated from the alkylate by filtration. The phosphorylation may be carried out using conventional techniques. The alkylate preferably comprises a minor proportion typically less than 20% of free phenol. This relatively low concentration of free phenol leads to the production of a liquid phosphate ester which has a relatively low content of triphenyl phosphate. Preferably the triaryl phosphate will comprise less than 10% more preferably less than 5% and most preferably less than 2% of triphenyl phosphate. Phosphates comprising less than 2% of triphenyl phosphates are described and claimed in U.S. Pat. No. 5,206,404. The present invention provides a method of producing these phosphates by alkylation of phenol, transalkylation and phosphorylation.

The invention is illustrated by the following examples:

Phosphorylation

Triaryl phosphate products were produced using the following conditions:

Phenolic feedstock was reacted with phosphorus oxychloride using a 0.06% $^w/_w$ magnesium chloride as catalyst. The phosphorus oxychloride was added to the phenolic feedstock between 120 and 160° C., and the reaction was completed by raising the temperature to 220° C. and sparging out HCl using nitrogen. The phenolic feedstocks and resultant triaryl phosphate products are given below:

Phenolic Feedstocks used in Phosphorylation Examples:

| Example No | Phenol % | m-TBP % | p-TBP % | di 2,4 TBP % | di 3,5 TBP % |
|---|---|---|---|---|---|
| 1 | 31.41 | 16.14 | 46.4 | 1.82 | 1.71 |
| 2 | 26.6 | 24.78 | 41.1 | 1.05 | 4.57 |
| 3 | 22.04 | 27.25 | 40.74 | 1.31 | 6.53 |
| 4 | 20.5 | 38.7 | 24.8 | 0.7 | 13.7 |
| 5 | 20.7 | 37.8 | 29.7 | 1.31 | 8.2 |
| 6 | 19.7 | 35.3 | 33.4 | 1 | 10.5 |
| 7 | 18.9 | 35.4 | 33.7 | 0.7 | 11.2 |
| 8 | 13.3 | 24.5 | 49.2 | 1.82 | 3.4 |
| 9 | 5.2 | 7.6 | 69.3 | 12.8 | 0.57 |

(All values are area % by GC)
m-TBP = meta tert-butyl phenol
p-TBP = para tert-butyl phenol
di 2,4 TBP = di 2,4 tert butyl phenol
di 3,5 TBP = di 3,5 tert butyl phenol The phenolic feedstocks above were reacted with phosphorus oxychloride to produce triaryl phosphate products. The results are given in the table below:
Triaryl Phosphate Products:

| Ex No | TPP % | mono m-tbp dpp % | mono p-tbp dpp % | di m-tbp pp % | di m/p-tbppp % | di p-tbp pp % | other di-tbpp % | tri m-tbpp % | tri m/p-tbpp % | tri p-tbpp % | other tri tbpp % | physical form of product |
|---|---|---|---|---|---|---|---|---|---|---|---|---|
| 1 | 4.76 | 9.2 | 14.34 | 5.68 | 18.39 | 14 | 5.73 | 5.62 | 8.88 | 4.59 | 3.06 | liquid |
| 2 | 3.13 | 7.16 | 12.16 | 5.31 | 18.48 | 15.51 | 6.18 | 6.87 | 11.8 | 6.62 | 4.2 | liquid |
| 3 | 1.93 | 5.79 | 8.83 | 5.67 | 17.62 | 13.44 | 7.96 | 8.64 | 13.4 | 6.98 | 7.63 | liquid |
| 4 | 1.77 | 7.67 | 5.04 | 11 | 15 | 4.9 | 17.3 | 10.62 | 7.1 | 1.5 | 15 | liquid |
| 5 | 1.63 | 5.5 | 6.7 | 6.4 | 16.85 | 10.8 | 9.6 | 9.9 | 13 | 6.6 | 9.56 | liquid |
| 6 | 1.67 | 6.56 | 6.6 | 8.42 | 17.35 | 8.6 | 11.8 | 10.9 | 11.1 | 4.1 | 10.8 | liquid |
| 7 | 1.2 | 5.6 | 5.5 | 8.2 | 16.6 | 8 | 12.5 | 11.7 | 11.6 | 4.4 | 12.7 | liquid |
| 8 | 0.44 | 2.1 | 4.1 | 3.1 | 12.6 | 12.6 | 5.8 | 9.7 | 19.8 | 13.6 | 10.7 | visc liquid |
| 9 | 1.3 | 0.2 | 1.3 | 0.2 | 3.16 | 13.6 | * | 2.1 | 18.5 | 51.9 | * | solid |

All values are area % by GC)
m-tbpdpp = meta tert butyl phenyl diphenyl phosphate
p-tbpdpp = para tert butyl phenyl diphenyl phosphate
m/p-tbpdpp = meta/para tert butyl phenyl diphenyl phosphate
di m-tbppp = di meta tert butyl phenyl diphenyl phosphate
di m/p-tbppp = di meta/para tert butyl phenyl diphenyl phosphate
di p-tbppp = di para tert butyl phenyl diphenyl phosphate
tri m-tbpp = tri meta tert butyl phenyl diphenyl phosphate
tri p-tbpp = tri para tert butyl phenyl diphenyl phosphate
tri m/p-tbpp = tri meta/para tert butyl phenyl diphenyl phosphate Examples 1, 2 and 3 demonstrate that a phenolic feedstock containing<22% phenol is required to generate a phosphate product containing<2% TPP.

Example 9 demonstrates that a phosphate produced from a phenolic feedstock with a low meta tert butyl phenol content is actually solid.

What is claimed is:

1. A process for producing a liquid triaryl phosphate ester of low triphenyl phosphate content and low viscosity comprising:
   (a) an alkylation and transalkylation stage wherein the alkylation and transalkylation take place concurrently in which a phenol is reacted with an olefin having 2 to 12 carbon atoms in the presence of a strong Bronsted acid catalyst having an acid strength of less than zero to give a reaction product comprising a mixture of meta and para alkylated phenols; said alkylation and transalkylation stage comprising combining the phenol with at least 0.8% w/w, based upon the weight of the phenol, of the strong acid catalyst and thereafter adding the olefin to provide the mixture of meta and para alkylated phenols and heating the mixture of alkylated phenols to increase the meta isomer content of the mixture to at least 20% whilst maintaining a phenol level below 22%; and
   (b) a phosphorylation stage wherein the mixture of alkylated phenols from the transalkylation stage is reacted with a phosphorylating agent.

2. A process according to claim 1 characterised in that the catalyst used in stage (a) has an acid strength of less than minus 3.

3. A process according to claim 2 characterised in that the catalyst has an acid strength of less than minus 8.

4. A process according to any of the preceding claims characterised in that the catalyst is an activated clay.

5. A process according to claim 4 characterised in that the catalyst is an acid activated bentonite, montmorillonite or Fullers Earth clay.

6. A process according to any of claims 1 to 3 characterised in that the catalyst is a heteropolyacid.

7. A process according to claim 6 characterised in that the catalyst is phosphotungstic acid.

8. A process according to claim 7 characterised in that the catalyst is a metal salt of phosphotungstic acid.

9. A process according to claim 1 wherein the alkylabon produces an alkylated phenol comprising at least 5% of meta alkyl phenol.

10. A process according to claim 1 wherein the alkylation and the transalkylation are carried out at a temperature of between 100° C. and 200° C.

11. A process according to claim 10 wherein the alkylation and the transalkylation are carried out at a temperature of between 150° C. and 180° C.

12. A process according to claim 1 characterised in that the reactants in the alkylation transalkylation stage are maintained at the reaction temperature for a period of at least 1 hour.

13. A process according to claim 12 characterised in that the reactants in the alkylation transalkylation stage are maintained at the reaction temperature until such time as the amount of meta alkylated phenol present comprises at least 25% by weight of the reaction mixture.

14. A process according to claim 1 wherein the olefin is propylene, n-butylene or isobutylene.

15. A process according to claim 1 wherein said strong acid catalyst includes a heterogeneous catalyst.

16. A process according to claim 15 wherein the heterogeneous catalyst is selected from the group consisting of: fluorided silica, fluorided alumina, silica supported phosphoric acid, silica supported sulphuric acid, diatomaceous earth supported phosphoric acid, diatomaceous earth supported sulphuric acid, sulphated zirconia, sulphated titania, and mixtures thereof.

17. A process according to claim 15 comprising separating the strong acid catalyst from the mixture of meta and para alkylated phenols by filtration.

18. A process according to claim 1 characterized in that the amount of catalyst use in the alkylation and transalkylation stage is at least 1.6% w/w based upon the weight of the phenol.

* * * * *

UNITED STATES PATENT AND TRADEMARK OFFICE
CERTIFICATE OF CORRECTION

| | |
|---|---|
| PATENT NO. | : 6,232,485 B1 |
| DATED | : May 15, 2001 |
| INVENTOR(S) | : Derbyshire et al. |

It is certified that error appears in the above-identified patent and that said Letters Patent is hereby corrected as shown below:

Column 8,
Line 53, please change "alkylabon" to -- alkylation --.

Signed and Sealed this

Twenty-third Day of April, 2002

Attest:

JAMES E. ROGAN
*Attesting Officer*   *Director of the United States Patent and Trademark Office*